United States Patent [19]

Petusky

[11] Plant 4,477

[45] Nov. 6, 1979

[54] CHRYSANTHEMUM NAMED HARTMANN'S YELLOW DIGNITY

[75] Inventor: Kerry S. Petusky, West Chicago, Ill.

[73] Assignee: Pan-American Plant Company, West Chicago, Ill.

[21] Appl. No.: 964,287

[22] Filed: Nov. 28, 1978

[51] Int. Cl.[2] ..... A01H 5/00

[52] U.S. Cl. ..... Plt./78

[58] Field of Search ..... Plt./77-78

*Primary Examiner*—Robert E. Bagwill

*Attorney, Agent, or Firm*—Chas. W. Rummler

[57] ABSTRACT

This chrysanthemum cultivar originated as a sport of the variety "Hartmann's Dignity" (U.S. Plant Pat. No. 4,377) and is distinguished by the pleasing light yellow color of its large composite and incurved standard blooms. Otherwise this new plant is about the same in its growth and blooming habits as the parent variety.

2 Drawing Figures

BACKGROUND OF THE NEW PLANT

My new variety of chrysanthemum was discovered by me at West Chicago, Ill., growing as a sport in a field of plants of the variety "Hartmann's Dignity" (U.S. Plant. Pat. No. 4,377) being grown in greenhouse for commercial purposes, as well as part of a continuous program carried on for the development of new and improved chrysanthemum varieties. The nature of this sport, as well as its distinctive color, led me to reproduce it as a new plant by means of cuttings from the original stem and subsequent propagation of the new plant by vegetative cuttings through several successive generations has shown its distinctive character to hold true and to appear to be firmly fixed. This has resulted in the new plant being selected for commercial exploitation and its propagation on a commercial scale is now being done at Parrish, Fla., as well as at West Chicago, Ill.

DESCRIPTION OF THE DRAWINGS

My new chrysanthemum cultivar is illustrated by the accompanying drawings, of which sheet one is a hand-colored photograph showing the form and color characteristics of the blossoms of the new plant, and sheet two is a mechanical reproduction of photocopies of typical leaves of the new plant taken at various stages of maturity.

DESCRIPTION OF THE NEW PLANT

The following is a detailed description of my new variety of chrysanthemum plant with color designations according to The R.H.S. Colour Chart of The Royal Horticultural Society of London, England, the observations having been made of greenhouse grown plants at West Chicago, Ill.

THE PLANT

Origin: Sport of "Hartmann's Dignity" (U.S. Plant Pat. No. 4,377).

Classification:

*Botanic.*—*Chrysanthemum morifolium.*

*Commercial.*—Standard incurved greenhouse cut flower type.

Form: Perennial herbaceous bush.

Height: 24 to 48 inches.

Growth: Vigorous and upright with very good strength and sturdy stems.

Branching: Normal when grown under natural conditions.

Foliage: Quantity — abundant with 7 to 9 leaves on 10 inches of stem length.

*Size of leaf.*—Length — about 4 to 8 inches. Width — about 2¼ to 4¾ inches.

*Leaf shape.*—Lobed, lanceolate and deeply serrated.

*Appearance.*—Canescent.

*Color.*—Upper side — 147A. Under side — 147B.

*Venation.*—Pinnate.

*Petioles.*—Length — ¾ to 1½ inches.

THE BUD

Form: Globular.

Size:

*Diameter.*—About ¾ inch.

*Depth.*—About ⅜ to ½ inch.

Opening rate: The bud opens slowly.

Color:

*When phyllaries first divide.*—5C.

*When florets begin to unfurl.*—Upper surface — 6B. Reverse surface — 6C.

Phyllaries: The receptacle bears many involucral bracts, which are spear-shaped and upstanding.

*Color.*—Inside surface — 146A; outside surface — 148A.

*Surface texture.*—Pubescent.

Peduncle: Erect and strong, about ¾ to 2½ inches in length.

*Surface texture.*—Pubescent.

THE FLOWER

Recommended flowering: Year around with photoperiod control.

Response: 9 week.

Natural flowering season: October 27 to November 4.

Flower type: Composite and incurved standard.

Borne: Naturally raceme; singly when disbudded.

Size: Very large.

*Diameter.*—About 5¼ to 6½ inches.

*Depth.*—About 4½ to 5 inches.

Shape: Flat when bloom first opens and becoming more globular as the bloom matures.

Petalage: The florets are numerous with capitulum arrangement.

*Form.*—Linear and incurved with obtuse apex.

*Texture.*—Soft.

*Appearance.*—Very slight shine.

*Color.*—Outer florets. Upper side — 4C. Reverse side — 4D. Inside florets: Upper side — 5B. Reverse side — 5D

Discoloration after full bloom:

*Outer florets.*—Upper side — 4D. Reverse side — 2D.

*Inner florets.*—Upper side — 3A. Reverse side — 3D.

Peduncle: Sturdy and upright; about 2½ inches long.

*Color.*—146B.

Persistence: Florets hang on and dry.

Fragrance: Typical chrysanthemum.

Lasting quality:

*On plant.*—3 weeks.

*As a cut flower.*—10 to 14 days.

REPRODUCTIVE ORGANS

Stamens: Number — 5.

*Arrangement.*—Syngenesious.

*Filaments.*—About 1/16 to ⅛ inch long.

*Color.*—Light yellow.

*Pollen.*—Color — yellow.

Pistils: One to each ray and disc floret.

*Styles.*—About ½ to 3/16 inch long.

*Stigma.*—Color — yellow.

Ovaries: Inferior, bicarpellate.

This new chrysanthemum variety is substantially the same as its parent "Hartmann's Dignity" as far as form and growth characteristics are concerned, the new plant being particularly distinguished by its yellow color.

I claim:

1. A new and distinct cultivar of chrysanthemum, substantially as herein shown and described, characterized by its unique yellow color when compared to the parent variety "Hartmann's Dignity".

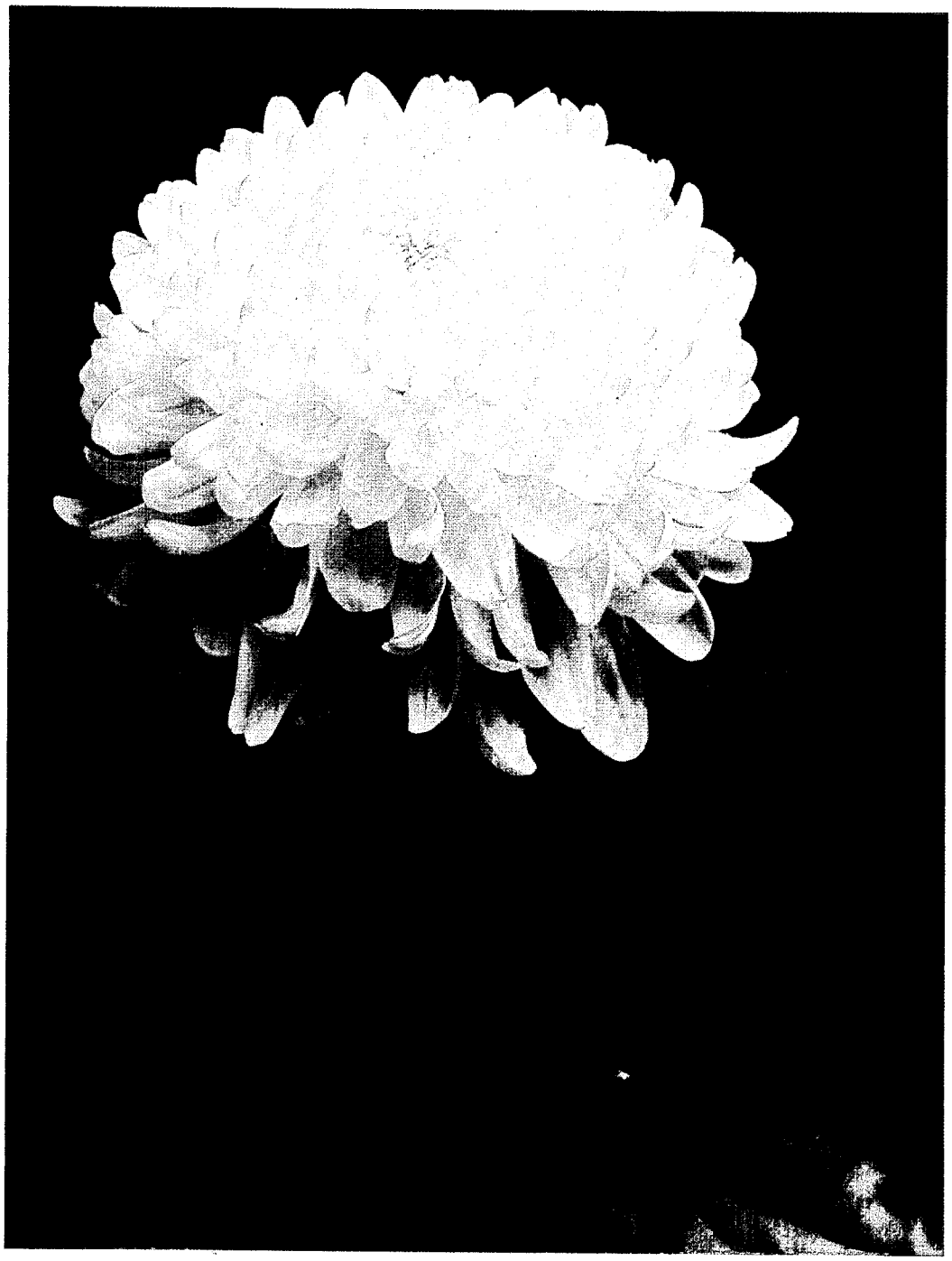

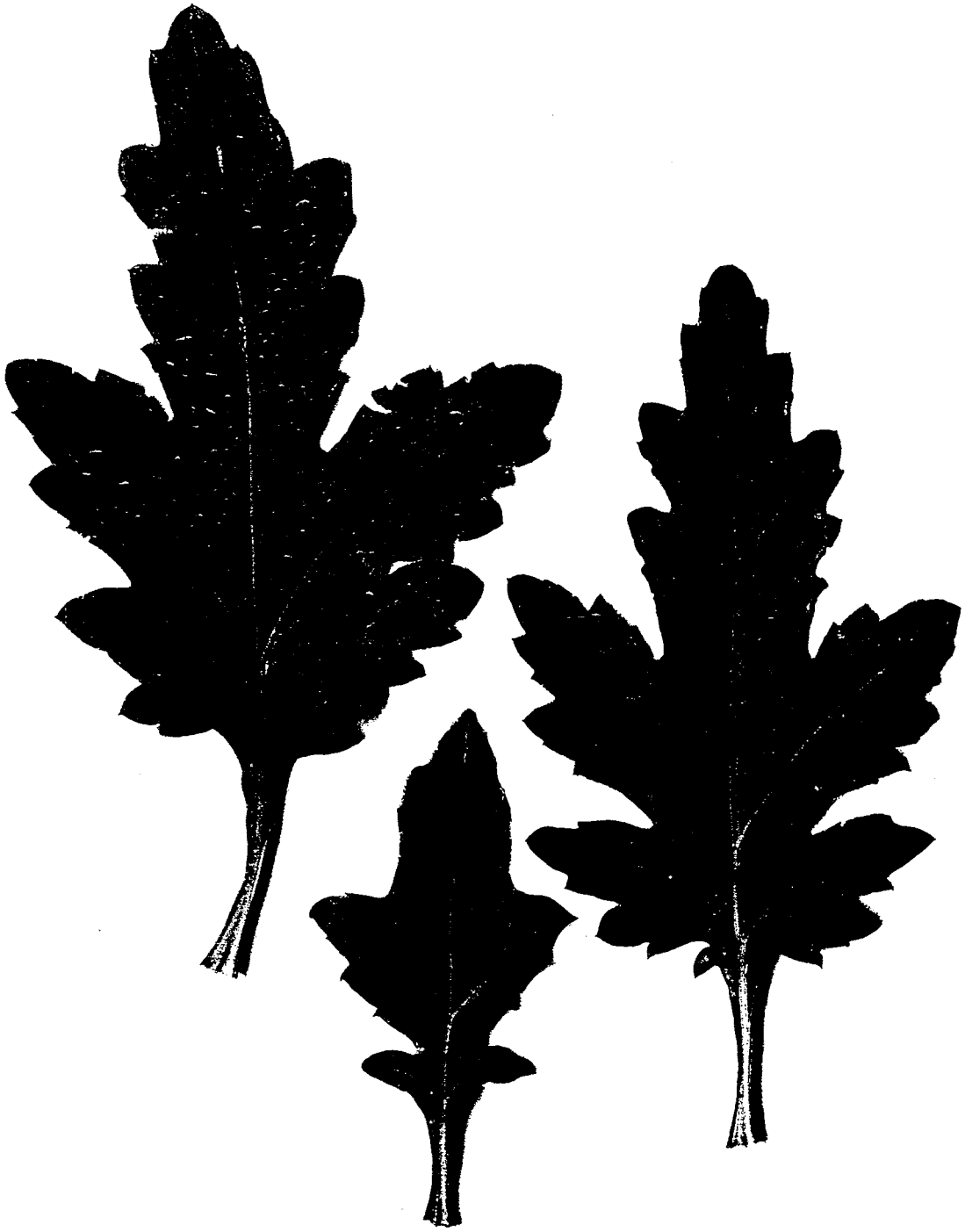

* * * * *